United States Patent [19]
Mineta et al.

[11] Patent Number: 5,482,651
[45] Date of Patent: Jan. 9, 1996

[54] DIOXANE TYPE LIQUID CRYSTAL SUBSTANCE

[75] Inventors: Hiroshi Mineta, Tsukuba; Tomoyuki Yui, Nagareyama; Yoshihiro Gocho; Takahiro Matsumoto, both of Tsukuba, all of Japan

[73] Assignee: Mitsubishi Gas Chemical Company, Inc., Tokyo, Japan

[21] Appl. No.: 25,571

[22] Filed: Mar. 3, 1993

[30] Foreign Application Priority Data

Mar. 4, 1992 [JP] Japan .................................. 4-047031

[51] Int. Cl.$^6$ .................. C09K 19/34; C07D 319/06
[52] U.S. Cl. .................. 252/299.61; 549/369
[58] Field of Search .................. 252/299.61; 549/369

[56] References Cited

U.S. PATENT DOCUMENTS

| | | | |
|---|---|---|---|
| 5,046,823 | 9/1991 | Mori et al. | 359/56 |
| 5,100,577 | 3/1992 | Bucheeker et al. | 252/299.01 |
| 5,171,471 | 12/1992 | Suzuki et al. | 252/299.61 |
| 5,238,598 | 8/1993 | Kurimoto et al. | 252/299.6 |
| 5,275,757 | 1/1994 | Mineta et al. | 252/299.61 |

FOREIGN PATENT DOCUMENTS

| | | |
|---|---|---|
| 0332392 | 9/1989 | European Pat. Off. |
| 545355A1 | 1/1992 | European Pat. Off. |

OTHER PUBLICATIONS

Week 8928, Derwent Publications Ltd., London, GB., AN 89–201,976 & JP-A-1,139,576 (Epson Corp.), Abstract.

(List continued on next page.)

Primary Examiner—Richard D. Lovering
Assistant Examiner—C. Harris
Attorney, Agent, or Firm—Sherman and Shalloway

[57] ABSTRACT

An antiferroelectric liquid crystal substance represented by the following general formula (1)

$$R-\text{[dioxane]}-\text{[phenyl]}-COO-X-COO-C^*H(Y)-(CH_2)_L(O)_mC_nH_{2n+1} \quad (1)$$

wherein R represents a straight-chain alkyl group of 6–10 carbon atoms; X represents

[phenyl] or [fluorophenyl];

when X is

[fluorophenyl],

Y is any of $CH_3$, $CF_3$ and $C_2H_5$, L is 0 or an integer of 5 to 8, m is 0 or 1, and n is an integer of 1 to 10; when X is

[phenyl],

Y is any of $CH_3$, $CF_3$ and $C_2H_5$, and (1) when Y is $CH_3$, L is 0 or an integer of 5 to 8, m is 0 or 1, and n is an integer of 1 to 10, (2) when Y is $CF_3$, L is an integer of 5 to 8, m is 1, and n is an integer of 1 to 10 and (3) when Y is $C_2H_5$, L is 0, m is 0, and n is an integer of 4–10.

24 Claims, 14 Drawing Sheets

OTHER PUBLICATIONS

Haramoto, "New Liquid Crystal Compounds (+)-4-Alkoxycarbonylphenyl-4-5-2-methylbutyl)1,3 . . . ", Molecular Crystals and Liquid Crystals, vol. 201, (1991), pp. 161–166, 1991.

Japanese Journal of Applied Physics, vol. 27, No. 5, (May 1988) pp. L729–L732.

Japanese Journal of Applied Physics, vol. 28, No. 7, (Jul. 1989) pp. L1265–L1268.

Japanese Journal of Applied Physics, vol. 28, No. 1, (Jan. 1989) pp. L119–L120.

Japanese Journal of Applied Physics, vol. 29, No. 1, (Jan. 1990) pp. 111–114.

JP–A–2133901, Mitsyoshi Ichihashi, "Ferroelectric Liquid Crystal Composition and Liquid Crystal Display Element", Aug. 28, 1989.

JP–A–316339, Giichi Suzuki, "Liquid Crystal Substance", Dec. 21, 1989.

JP–A–316367, Giichi Suzuki, "Liquid Crystal Substance Having Heterocyclic Skeleton", Dec. 21, 1989.

JP–A–316372, Giichi Suzuki, "Dioxane–Based Liquid Crystal Substance", Dec. 21, 1989.

JP–A–28128/90, Giichi Suzuki, et al., "Liquid Crystal Compounds Containing Naphthalene Nucleus", Apr. 28, 1989.

Liquid Crystals, vol. 6, No. 2 (1989) pp. 167–174, "New Fluorine–Containing Ferroelectric Liquid Crystal Compounds Showing Tristable . . . ".

DIOXANE TYPE LIQUID CRYSTAL SUBSTANCE

FIELD OF THE INVENTION

The present invention relates to a novel dioxane type antiferroelectric liquid crystal substance.

BACKGROUND OF THE INVENTION

Liquid crystal display devices have been used in various small-sized display devices because they are operated at a low voltage, low consumption of electric power and being enable thin display. Meanwhile, with the recent utilization of liquid crystal display devices in wider applications such as apparatuses for office automation, televisions and the like, there has rapidly arisen a requirement for high-performance large-sized liquid crystal display device having such display capacity and display quality as to surpass those of conventional CRT display devices. However, even in the case of active matrix-driven liquid crystal display devices now employed in liquid crystal televisions, their modification into a large-sized device of low cost is not easy owing to the complex production process and low yield, as long as a currently used nematic liquid crystal is employed therein. Also, in the case of simple matrix-driven STN type liquid crystal display devices, the driving in large capacity is not easy; the response time has a limitation; and the video rate display is difficult. Thus, nematic liquid crystal display devices are unable to satisfy the above requirement for high-performance liquid crystal display device.

Under such a situation, attention is being paid to a liquid crystal display device using a ferroelectric liquid crystal substance, which is a quick response liquid crystal display device. The surface-stabilized ferroelectric liquid crystal (SSFLC) device reported by N. A. Clark and S. T. Lagerwall is drawing attention because of the quick response (which has been unobtainable with conventional liquid crystal display devices) and wide viewing angle, and the switching property has been studied in detail. A number of SSFLC substances are in actual production for use in SSFLC devices of desired properties. However, these SSFLC substances have various problems. For example, they have an insufficient threshold; they have poor contrast because, for example, their layer structure is a chevron structure; they show no quick response; their alignment is difficult to control and their bistability (this is one of the biggest characteristics of SSLFC) is difficult to achieve; and their alignment is destructed by mechanical impact and its recovery is difficult.

Devices employing switching mechanisms different from that of SSFLC are also being developed simultaneously. The switching between three stable states, of a liquid crystal substance having an antiferroelectric phase (said substance is hereinafter referred to as antiferroelectric liquid crystal substance) is one of such new switching mechanisms (Japanese Journal of Applied Physics, Vol. 27, p. L729, 1988).

Antiferroelectric liquid crystal substances each have three stable states, i.e. the same two uniform states (Ur, Ue) as seen in ferroelectric liquid crystal substances and a third state. That this third state is an antiferroelectric phase, was reported by Japanese Journal of Applied Physics, Vol. 28, p. L1265, 1989). Such switching between three stable states is the first characteristics of antiferroelectric liquid crystal substances. The second characteristic of antiferroelectric liquid crystal substances is that each of them has a clear threshold for an applied voltage. The third characteristic of ferroelectric liquid crystal substances is that they have good memory effect. By using an antiferroelectric liquid crystal substance having these excellent characteristics, there can be achieved a liquid crystal display device giving quick response and good contrast.

As another important characteristic of antiferroelectric liquid crystal substances, there can be mentioned a fact that their layer structure can be easily switched by an electric field (Japanese Journal of Applied Physics, Vol. 28, p. L119, 1989, Japanese Journal of Applied Physics, Vol. 29, p. L111, 1990). Owing to this fact, it becomes possible to produce a liquid crystal display device having little defects and having self-recoverability of alignment and consequently produce a liquid crystal display device capable of giving excellent contrast. As the antiferroelectric liquid crystal display devices, there are known those described in Japanese Patent Application Kokai (Laid-Open) Nos. 213390/1989, 316339/1989, 316367/1989, 316372/1989 and 28128/1990 and Liquid Crystals, Vol. 6, p. 167, 1989. Owing to the short history of studies on antiferroelectric liquid crystal substances, the number of hitherto known antiferroelectric liquid crystal substances is not large as compared with the number of ferroelectric liquid crystal substances, but the number of on the increase with the progress of said studies.

When the antiferroelectric liquid crystal substances produced heretofore are looked from the response time, many of them are not sufficient in response time and the number of said substances applicable to in the same manner as in Example 1 (8). As a result, the display devices capable of giving a fine and precise image is not so large. The antiferroelectric liquid crystal substances have been slightly disadvantageous in this point, as compared with conventional ferroelectric liquid crystal substances. Therefore, if there can be developed an antiferroelectric liquid crystal substance giving very quick response at room temperature or thereabouts, it is very advantageous for the realization of a display device capable of giving a fine and precise image. The present invention has been made under such a circumstance and provides an antiferroelectric liquid crystal substance giving very quick response at room temperature or thereabouts.

OUTLINE OF THE INVENTION

Figure 1:
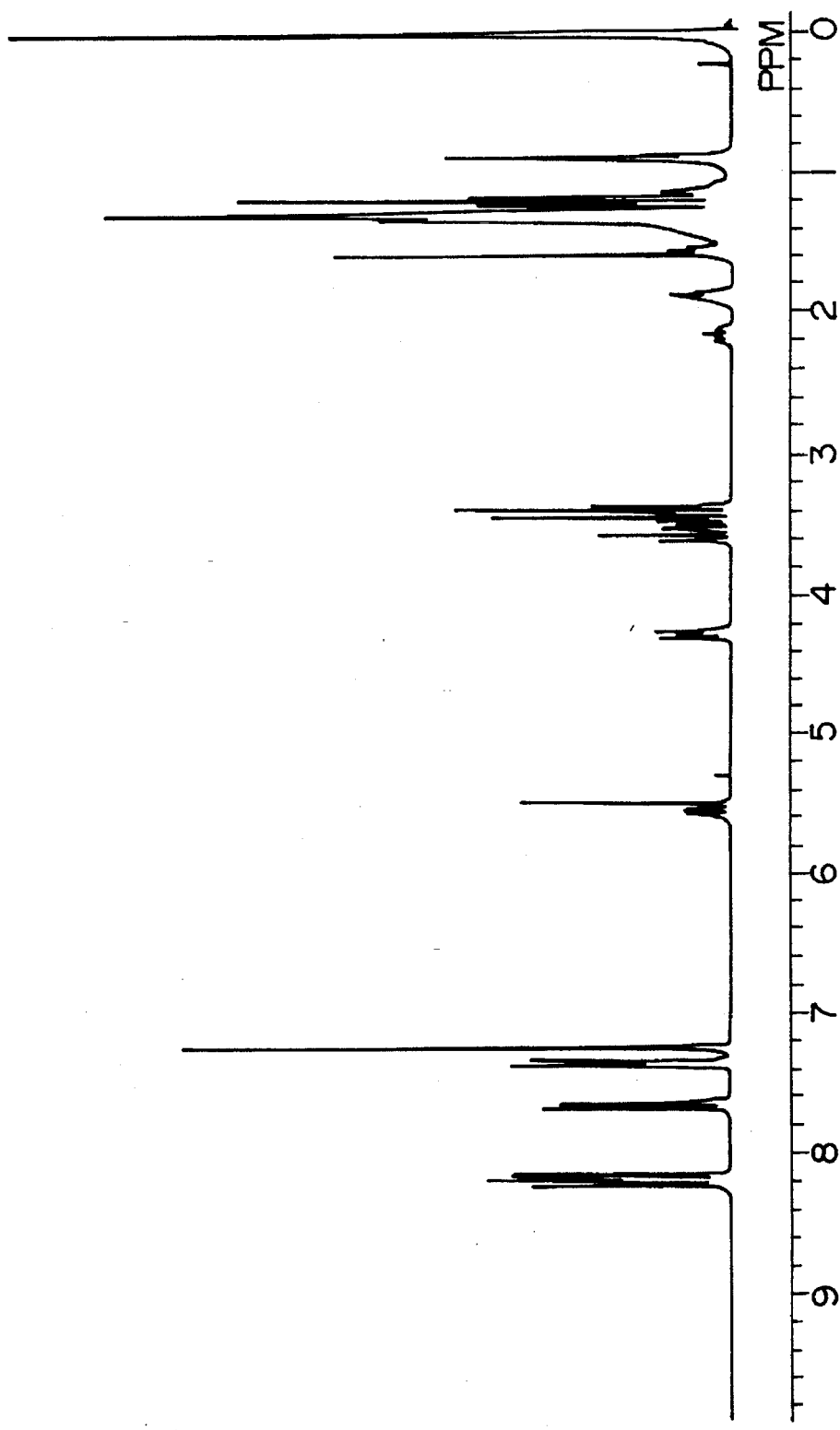
FIG. 1 is an NMR spectrum of the liquid crystal substance obtained in Example 1.

The present invention provides a novel antiferroelectric liquid crystal substance represented by the following general formula (1)

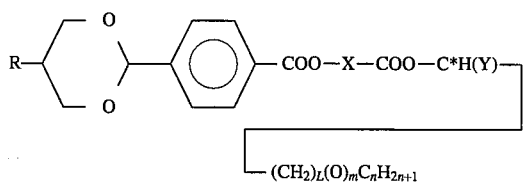

wherein R represents a straight-chain alkyl group of 6–10 carbon atoms; X represents

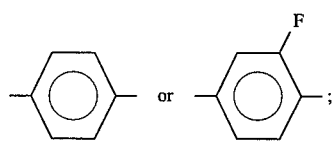

when X is

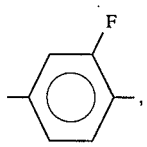

Y is any of $CH_3$, $CF_3$ and $C_2H_5$, L is 0 or an integer of 5 to 8, m is 0 or 1, and n is an integer of 1 to 10; when X is

Y is any of $CH_3$, $CF_3$ and $C_2H_5$, and (1) when Y is $CH_3$, L is 0 or an integer of 5 to 8, m is 0 or 1, and n is an integer of 1 to 10, (2) when Y is $CF_3$, L is an integer of 5 to 8, m is 1, and n is an integer of 1 to 10 and (3) when Y is $C_2H_5$, L is 0, m is 0, and n is an integer of 4–10.

In the general formula (1), C* refers to an asymmetric carbon atom.

Of the optically active alcohols used in the present invention, for those such as R-(+)-1,1,1-trifluoro-2-octanol and S-(+)-3-nonanol, there were used commercial products. Optically active alcohols such as R-(+)-1,1,1-trifluoro-7-ethoxy-2-heptanol can be produced as follows.

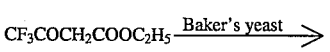

$$CF_3C*H(OH)CH_2COOC_2H_5 \xrightarrow{DHP} CF_3C*HCH_2COOC_2H_5 \text{ (O—THP)} \quad (b)$$

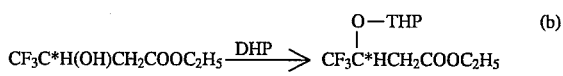

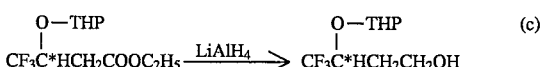

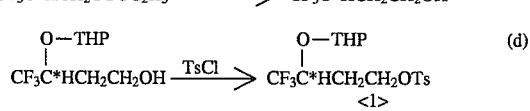

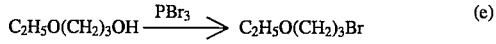

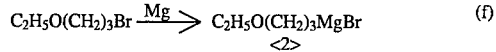

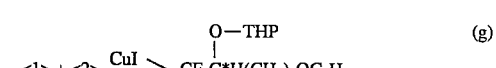

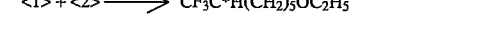

In the above reaction formulas, THP refers to a tetrahydropyranyl group; Ts refers to a paratoluenesulfonyl group; DHP refers to dihydropyran; and C* refers to an asymmetric carbon atom.

The process for producing an intended compound of the present invention can be shown by, for example, the following reaction formulas.

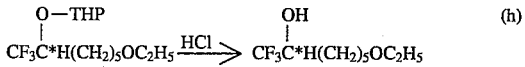

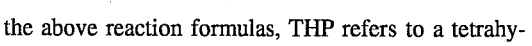

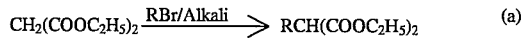

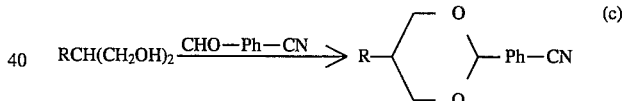

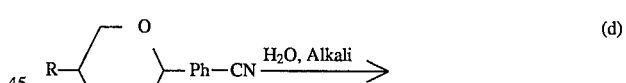

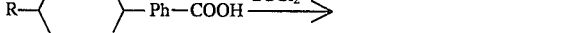

-continued $$CH_3COO-X-COO-C^*H(CF_3)(CH_2)_L(O)_mC_nH_{2n+1}$$

(h)

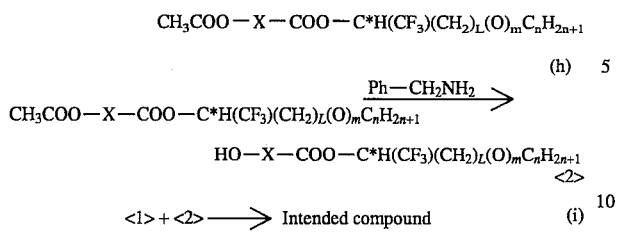

$$\langle 1 \rangle + \langle 2 \rangle \longrightarrow \text{Intended compound}$$ (i)

In the above reaction formulas, Ph refers to a phenyl group and C* refers to an asymmetric carbon atom.

The present invention can provide a novel antiferroelectric liquid crystal substance which gives very quick response at room temperature or thereabouts, which is switchable between three stable states, which has a clear threshold, and which has good memory effect. Therefore, said antiferroelectric liquid crystal substance can be used in liquid crystal display devices utilizing the above properties of the substance.

The present invention is hereinafter described more specifically referring to Examples and Comparative Examples. However, the present invention is not restricted thereto.

Production of 4-(1-trifluoromethyl-8-ethoxy-octyloxycarbonyl)phenyl 4-(5-n-octyl-1,3-dioxan-2-yl)-benzoate [a compound of general formula (1) wherein R= n-$C_8H_{17}$, X=shown in Table 1, Y=-$CF_3$, L=7, m=1 and n=2]

(1) Production of ethyl octylmalonate

In a 1-liter four-necked flask was placed 200 ml of ethanol. Thereto was added 7.6 g of finely cut metallic sodium in small portions to prepare sodium ethoxide. Thereto were dropwise added 54.6 g of diethyl malonate and 63.9 g of octyl bromide in this order. The mixture was refluxed for 3 hours. Then, the most part of ethanol was removed by distillation at normal pressure. To the residue was added 200 ml of water, and the mixture was subjected to extraction with 250 ml of ether. The ether solution was dried over sodium sulfate; ether was removed therefrom by distillation; the residue was subjected to vacuum distillation to obtain 72.1 g of a colorless oily substance having a boiling point of 111° C. at 2 mmHg. Yield: 85%

(2) Production of 2-octyl-1,3-propanediol

In a 1-liter four-necked flask were placed 250 ml of ether and 19.0 g of lithium aluminum hydride. Thereto was dropwise added a solution of 72.1 g of the diethyl octylmalonate produced in the above (1), dissolved in 50 ml of ether, at such a rate that ether could be refluxed gently. Then, the mixture was subjected to refluxing for 3 hours. After cooling of the reaction mixture, a water-THF mixture was added to the reaction mixture to decompose excessive lithium aluminum hydride. The solid in the resulting liquid was removed by filtration. The filtrate was washed with a saturated aqueous sodium chloride solution and dried over anhydrous sodium sulfate. The solvent in the resulting liquid was removed to obtain crude crystals. The crude crystals were recrystallized from isooctane to obtain 32.4 g of colorless crystals. Yield: 65%

(3) Production of 4-(5-octyl-1,3-dioxan-2-yl)benzonitrile

In a 500-ml eggplant-shaped flask were placed 32.3 g of 2-octyl-1,3-propanediol, 22.5 g of p-cyanobenzaldehyde, 0.11 g of p-toluenesulfonic acid monohydrate and 300 ml of benzene. They were heated. The resulting water was removed by azeotropy with benzene. Then, benzene was removed by distillation. To the residue was added an aqueous sodium hydrogencarbonate solution for neutralization. The resulting liquid was subjected to extraction with dichloromethane. The extract was washed with water and then dried over anhydrous sodium sulfate. Dichloromethane was removed by distillation to obtain a solid. The solid was recrystallized from isooctane to obtain 37.7 g of colorless crystals.

(4) Production of 4-(5-octyl-1,3-dioxan-2-yl)benzoic acid

In a 2-liter eggplant-shaped flask equipped with a condenser were placed 27.2 g of potassium hydroxide, 20 ml of water, 1 liter ethylene glycol and 36.6 g of the benzonitrile obtained in the above (3). They were heated at 180° C. for 6 hours. 1 N hydrochloric acid was added to the reaction mixture to make it acidic. The resulting precipitate was collected by filtration, water-washed and air-dried. The resulting solid was recrystallized from ethanol to obtain 17.5 g of an intended benzoic acid derivative.

(5) Production of 4-acetoxy-1-(1-trifluoromethyl-8-ethoxy-octyloxycarbonyl)benzene 1.2 g of 4-acetoxy-benzoic acid was added to 20 ml of thionyl chloride. The mixture was subjected to a reaction for 5 hours under reflux. Excessive thionyl chloride was removed by distillation. To the residue was dropwise added a mixture of 3 ml of pyridine, 20 ml of toluene and 0.6 g of R-(+)-1,1,1-trifluoro-9-ethoxy-2 -nonanol. After the dropwise addition, the mixture was stirred at room temperature for 24 hours and then diluted with 50 ml of dichloromethane. The organic layer was washed with diluted hydrochloric acid, a 1 N aqueous sodium hydroxide solution and water in this order, and dried over sodium sulfate. The solvent in the resulting liquid was removed by distillation, and the resulting crude compound was purified by silica gel column chromatography using hexane/ethyl acetate as a solvent, to obtain 1.2 g of an intended compound.

(6) Production of 4-hydroxy-(1-trifluoromethyl-8-ethoxy-octyloxycarbonyl)benzene 1.2 g of the above compound was dissolved in 30 ml of ethanol. Thereto was dropwise added 0.8 g of benzylamine. The mixture was stirred at room temperature for 24 hours, then diluted with 50 ml of dichloromethane, washed with diluted hydrochloric acid and water in this order, and dried over sodium sulfate. The solvent in the resulting liquid was removed by distillation. The residue was isolated and purified by silica gel column chromatography to obtain 1.0 g of an intended compound.

(7) Production of 4-(1-trifluoromethyl-8-ethoxyoctyloxycarbonyl)phenyl 4-(5-octyl-1,3-dioxan-2-yl)benzoate 10 ml of thionyl chloride was added to 1.0 g of the benzoic acid derivative obtained in the above (4), and the mixture was subjected to refluxing for 5 hours. Excessive thionyl chloride was removed by distillation. To the residue were added 2 ml of pyridine and 15 ml of toluene. Thereto was dropwise added 0.6 g of the compound obtained in the above (6), and the mixture was subjected to a reaction at room temperature for 24 hours. After the completion of the reaction, the reaction mixture was diluted with 50 ml of dichloromethane. The dilution product was washed with diluted hydrochloric acid, a 1 N aqueous sodium carbonate solution and water in this order. The organic layer was dried over sodium sulfate. The solvent in the resulting liquid was removed by distillation. The residue was subjected to silica gel chromatography to obtain 1.0 g of a final compound. The NMR spectrum of the compound is shown in FIG. 1. The identification of the phases of the compound was conducted by texture observation and DSC.

The phase sequence of the compound was as follows. The compound was confirmed to be a liquid crystal substance having an antiferroelectric phase.

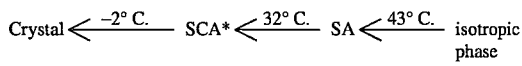

In the above phase sequence, SA refers to a smectic A phase and SCA* refers to an antiferroelectric phase.

Figure 2:
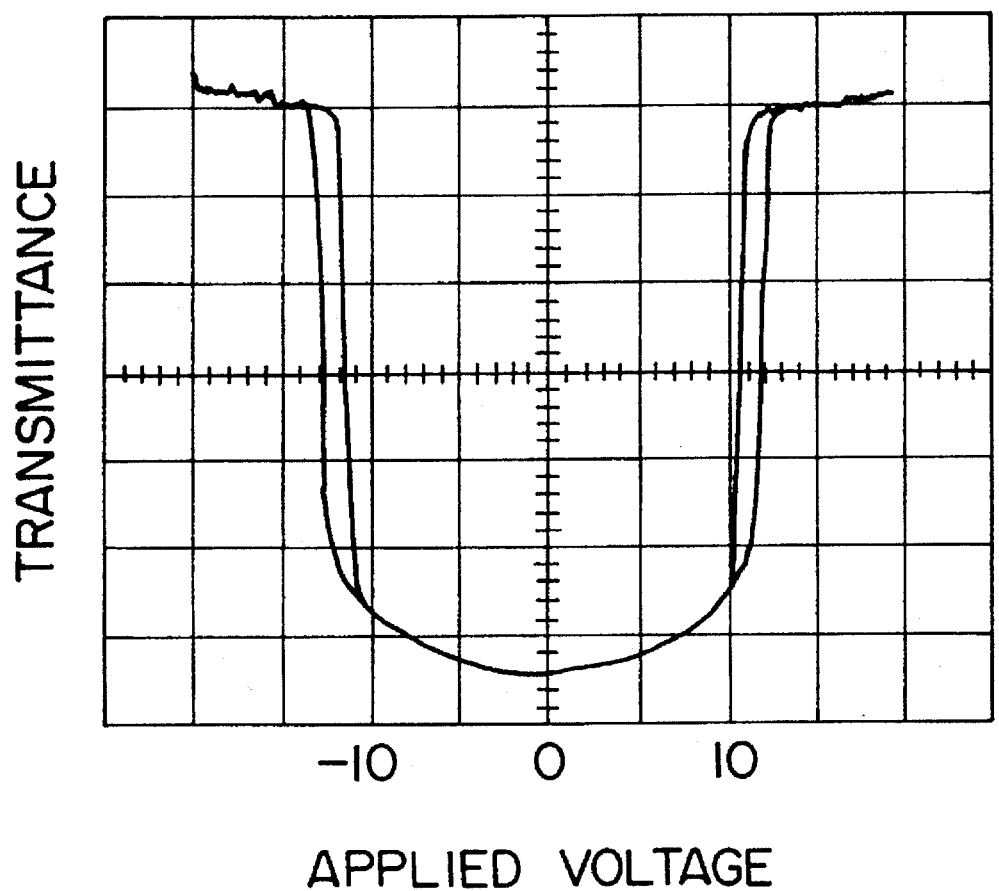
FIG. 2 is an optical response hysteresis of the liquid crystal substance obtained in Example 1.

(8) The above compound was filled, in the isotropic phase, into a liquid crystal cell (cell thickness: 2 μm) with ITO electrodes, having a polyimide thin film subjected to a rubbing treatment. The cell was slowly cooled at a rate of 1.0° C. per minute to align the compound in the SA phase. Then, the cell was placed between an analyzer and a polarizer perpendicularly intersecting each other, in such a way that the crystal direction of the liquid crystal became parallel to the analyzer or the polarizer. A triangular wave voltage of ±40 V and 0.2 Hz was applied to the cell and the change of transmittance was measured using a photomultiplier. As a result, double hysteresis characteristic of an antiferroelectric phase was seen in a temperature range from 32° C. to −1° C. The optical response hysteresis at 30° C. is shown in FIG. 2.

Further, a rectangular wave voltage of 30 Hz (frequency) and 35 V was applied stepwise to the above liquid crystal cell, and the response time was measured (the response time was defined as a time required for the transmittance to change from 10% to 90%). The response time at 25° C. was 123 microseconds from the antiferroelectric phase to the ferroelectric phase and 99 microseconds from the ferroelectric phase to the antiferroelectric phase, and the response was very quick.

EXAMPLE 2

Production of 4-(1-ethyl-heptyloxycarbonyl)phenyl 4-(5-n-octyl-1,3-dioxan-2-yl)benzoate [a compound of general formula (1) where R=n-$C_8H_{17}$, X=shown in Table 1, Y=-$C_2H_5$, L=0, m=0 and n=6]

An intended compound was produced in the same manner as in Example 1 except that the R-(+)-1,1,1-trifluoro-9-ethoxy-2-nonanol used in Example 1 was replace by S-(+)-3-nonal.

Figure 3:
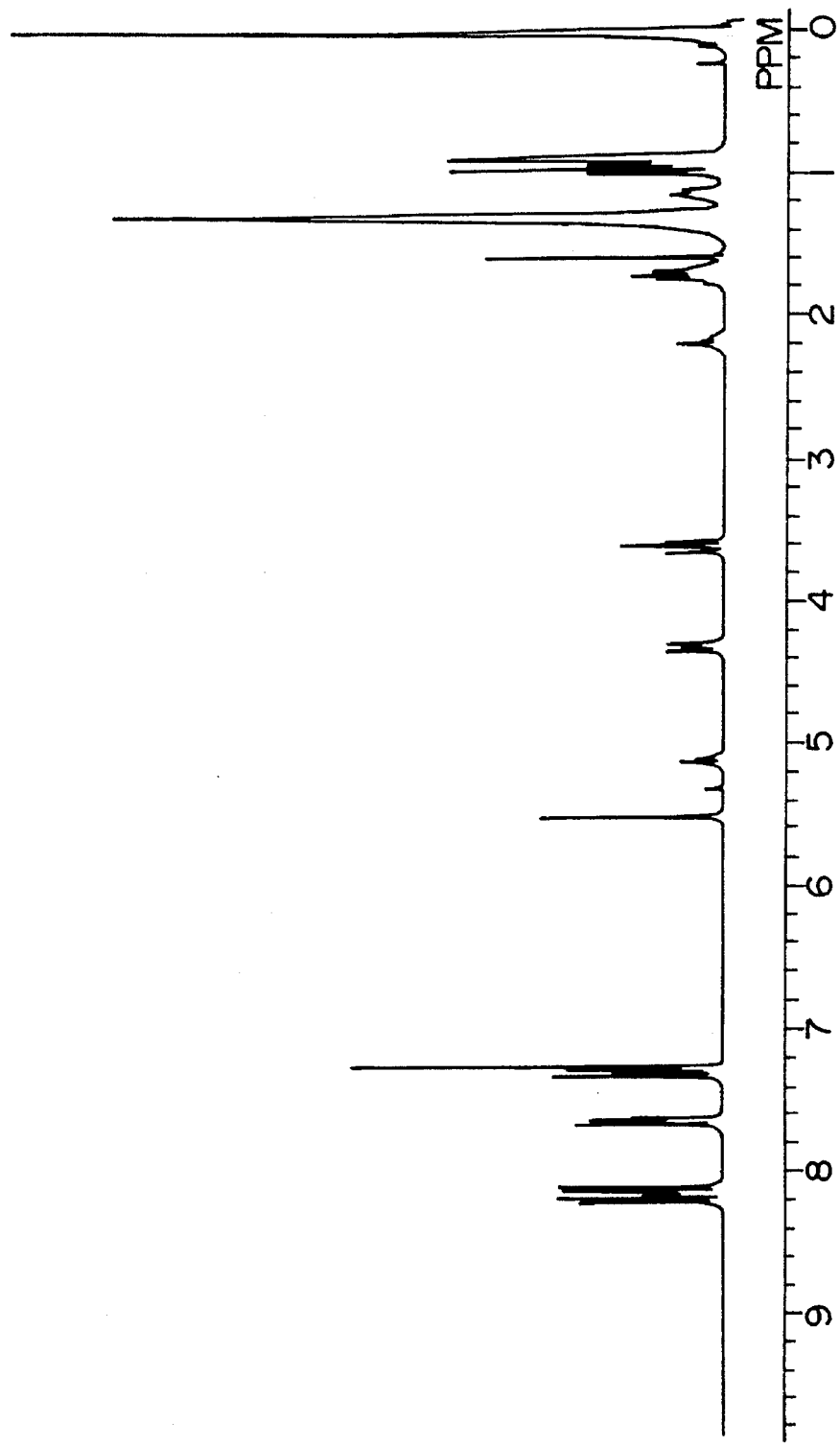
FIG. 3 is an NMR spectrum of the liquid crystal substance obtained in Example 2.

The NMR spectrum of the compound is shown in FIG. 3. The identification of the phase of the compound was conducted by texture observation and DSC. The measurement of the melting point of the compound was conducted by DSC, and the melting point was 61° C.

The phase sequence of the compound was as follows. The compound was confirmed to be a liquid crystal substance having an antiferroelectric phase.

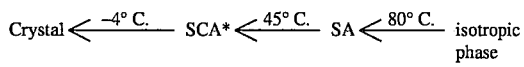

The compound was examined for optical response in the same manner as in Example 1 (8). As a result, the compound showed double hysteresis characteristic of an antiferroelectric phase at a temperature range or 70° C. to −3° C. The compound was also examined for response time in the same manner as in Example 1 (8). As a result, the response time at 35° C. was 45 microseconds from the antiferroelectric phase to the ferroelectric phase and 29 microseconds from the ferroelectric phase to the antiferroelectric phase, and the response was very quick.

COMPARATIVE EXAMPLE 1

Production of 4-(1-methyl-6-ethoxy-hexyloxycarbanol)phenyl 4-(5-n-octyl-1,3-dioxan-2-yl)benzoate [a compound of general formula (1) wherein R=n-$C_8H_{17}$, X= shown in Table 2, Y=-$CH_3$, L=5, m=1 and n=2]

An intended compound was produced in the same manner as in Example 1 except that the R-(+)-1,1,1-trifluoro-9-ethoxy-2-nonanol used in Example 1 was replaced by (+)-7-nonal-ethoxy-2-heptanol.

Figure 4:
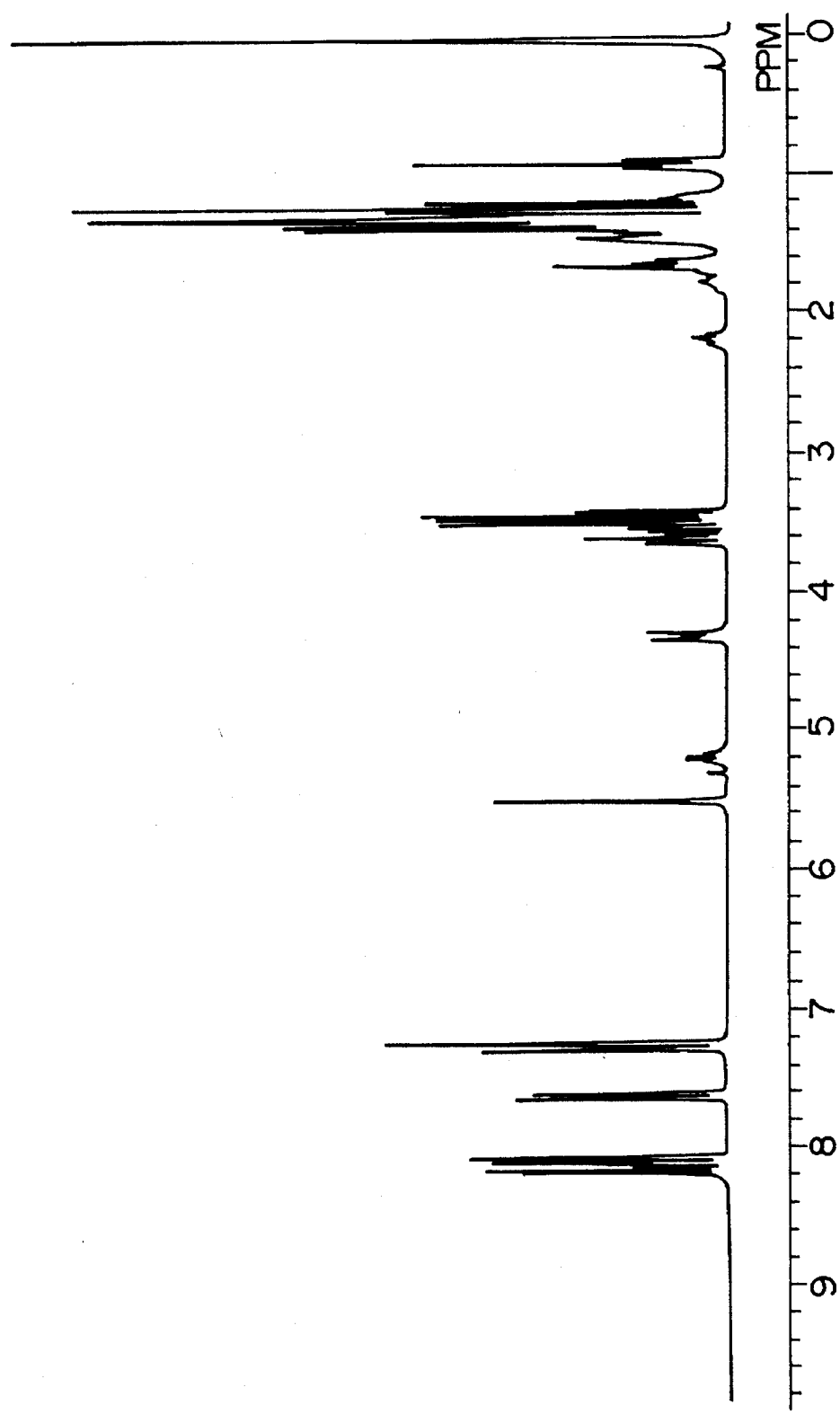
FIG. 4 is an NMR spectrum of the liquid crystal substance obtained in Comparative Example 1.

The NMR spectrum of the compound is shown in FIG. 4. The identification of the phase of the compound was conducted by texture observation and DSC. The measurement of the melting point of the compound was conducted by DSC, and the melting point was 67° C.

The phase sequence of the compound was as follows. The compound had no antiferroelectric phase.

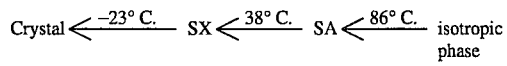

In the above phase sequence, SX refers to an unidentified phase.

EXAMPLE 3

Production of 3-fluoro-4-(1-trifluoromethyl-6-ethoxy-hexyloxycarbonyl)phenyl 4-(5-n-octyl-1,3-dioxan-2-yl)benzoate [a compound of general formula (1) wherein R= n-$C_8H_{17}$, X=shown in Table 1, Y=-$CF_3$, and L=5, m=1 and n=2]

An intended compound was produced in the same manner as in Example 1 except that the R-(+)-1,1,1-trifluoro-9-ethoxy-2-nonanol used in Example 1 was replaced by R-(+)-1,1,1-trifluoro-7-ethoxy-2-heptanol and the 4-acetoxy-benzoic acid used in Example 1 was replaced by 2-fluoro-4-acetoxy-benozoic acid.

Figure 5:
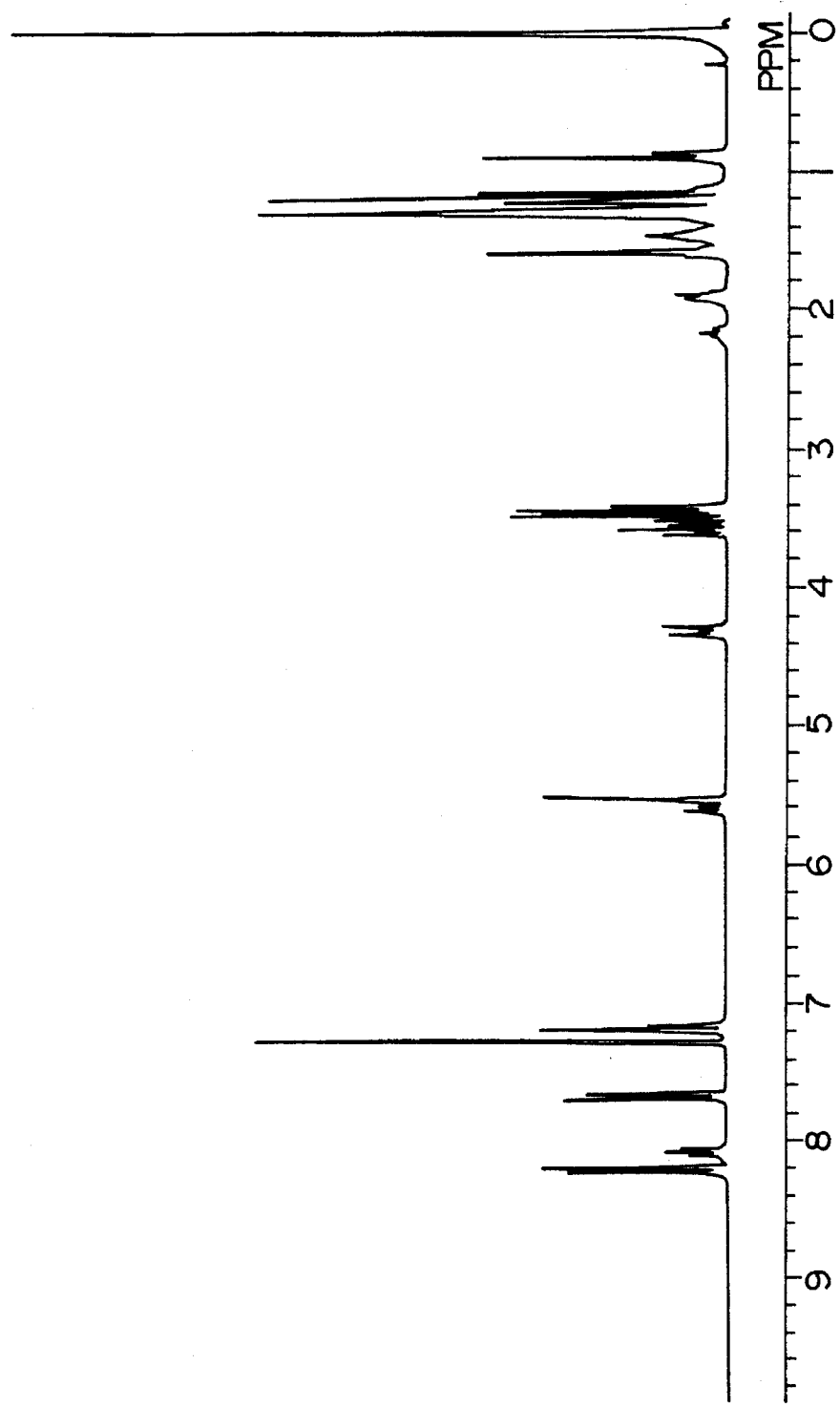
FIG. 5 is an NMR spectrum of the liquid crystal substance obtained in Example 3.

The NMR spectrum of the compound is shown in FIG. 5. The identification of the phase of the compound was conducted by texture observation and DSC.

The phase sequence of the compound was as follows. The compound was confirmed to be a liquid crystal substance having an antiferroelectric phase.

The compound was examined for optical response in the same manner as in Example 1 (8). As a result, the compound showed double hysteresis characteristic of an antiferroelectric phase at a temperature range or 38° C. to −20° C. The compound was also examined for response time in the same manner as in Example 1 (8). As a result, the response time at 28° C. was 100 microseconds from the antiferroelectric phase to the ferroelectric phase and 240 microseconds from the ferroelectric phase to the antiferroelectric phase, and the response was very quick.

EXAMPLE 4

Production of 3-fluoro-4-(1-trifluoromethyl-8-ethoxy-hexyloxycarbonyl)phenyl 4-(5-n-octyl-1,3-dioxan-2-yl)benzoate [a compound of general formula (1) wherein R=n-$C_8H_{17}$, X=shown in Table 1, Y=-$CF_3$, L=7, m=1 and n=2]

An intended compound was produced in the same manner as in Example 3 except that the R-(+)-1,1,1-trifluoro-7-ethoxy-2-heptanol used in Example 3 was replaced by R-(+)-1,1,1-trifluoro-9-ethoxy-2-nonanol.

Figure 6:
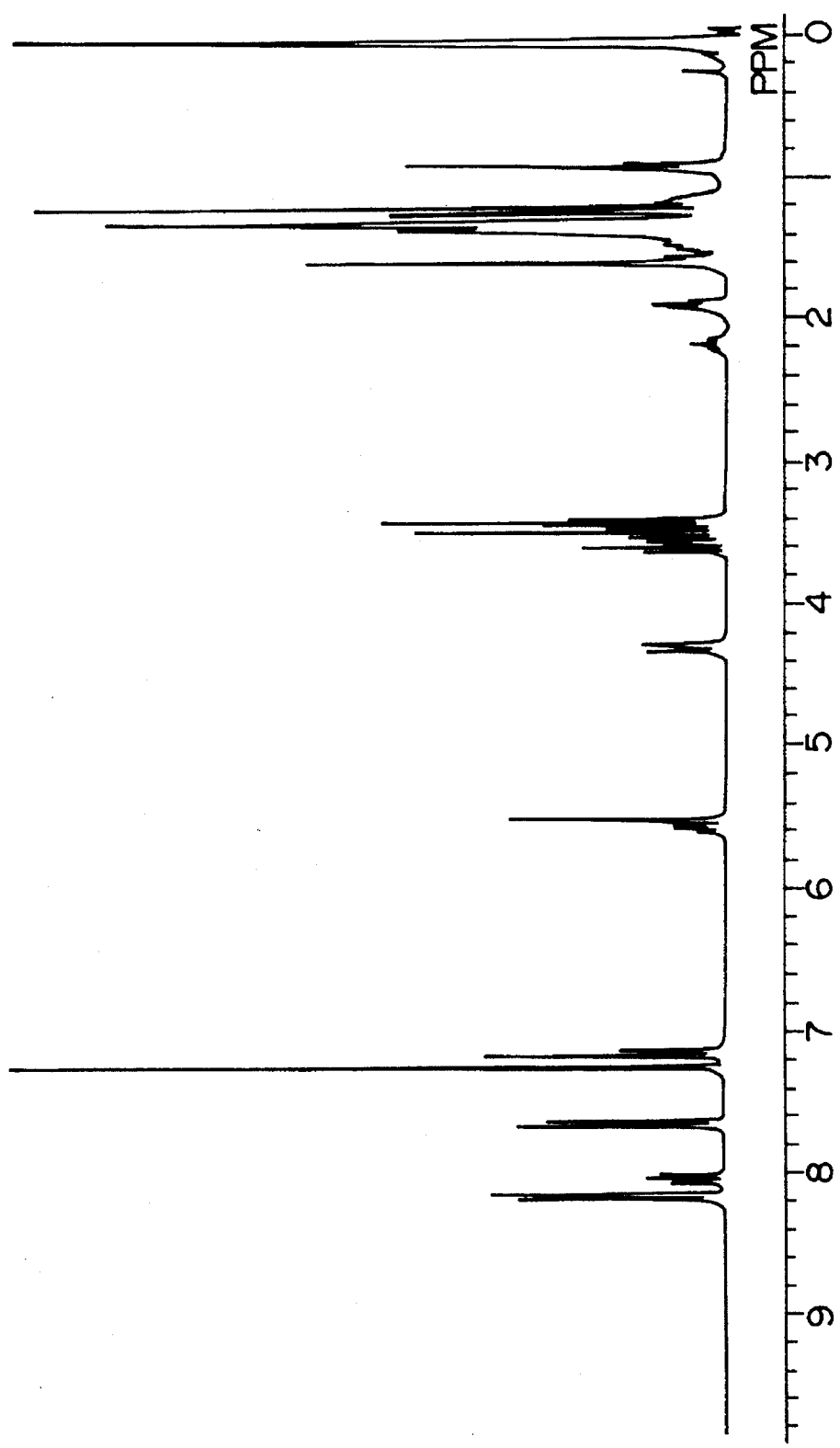
FIG. 6 is an NMR spectrum of the liquid crystal substance obtained in Example 4.

The NMR spectrum of the compound is shown in FIG. 6. The identification of the phases of the compound was conducted by texture observation and DSC.

The phase sequence of the compound was as follows. The compound was confirmed to be a liquid crystal substance having an antiferroelectric phase.

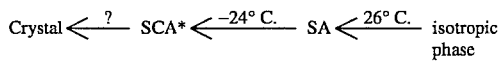

The compound was examined for optical response in the same manner as in Example 1 (8). As a result, the compound showed double hysteresis characteristic of an antiferroelectric phase 24° C. or below. The compound was also examined for response time in the same manner as in Example 1 (8). As a result, the response time at 15° C. was 428 microseconds from the antiferroelectric phase to the ferroelectric phase and 212 microseconds from the ferroelectric phase to the antiferroelectric phase, and the response was very quick.

EXAMPLE 5

Production of 3-fluoro-4-(1-trifluoromethylheptyloxycarbonyl)phenyl 4-(5-n-octyl-1,3-dioxan-2-yl)benzoate [a compound of general formula (1) wherein R =n-$C_8H_{17}$, X=shown in Table 1, Y=-$CF_3$, L=0, m=0 and n=6]

An intended compound was produced in the same manner as in Example 3 except that the R-(+)-1,1,1-trifluoro-7-ethoxy-2-heptanol used in Example 3 was replaced by R-(+)-1,1,1-trifluoro-2-octanol.

Figure 7:
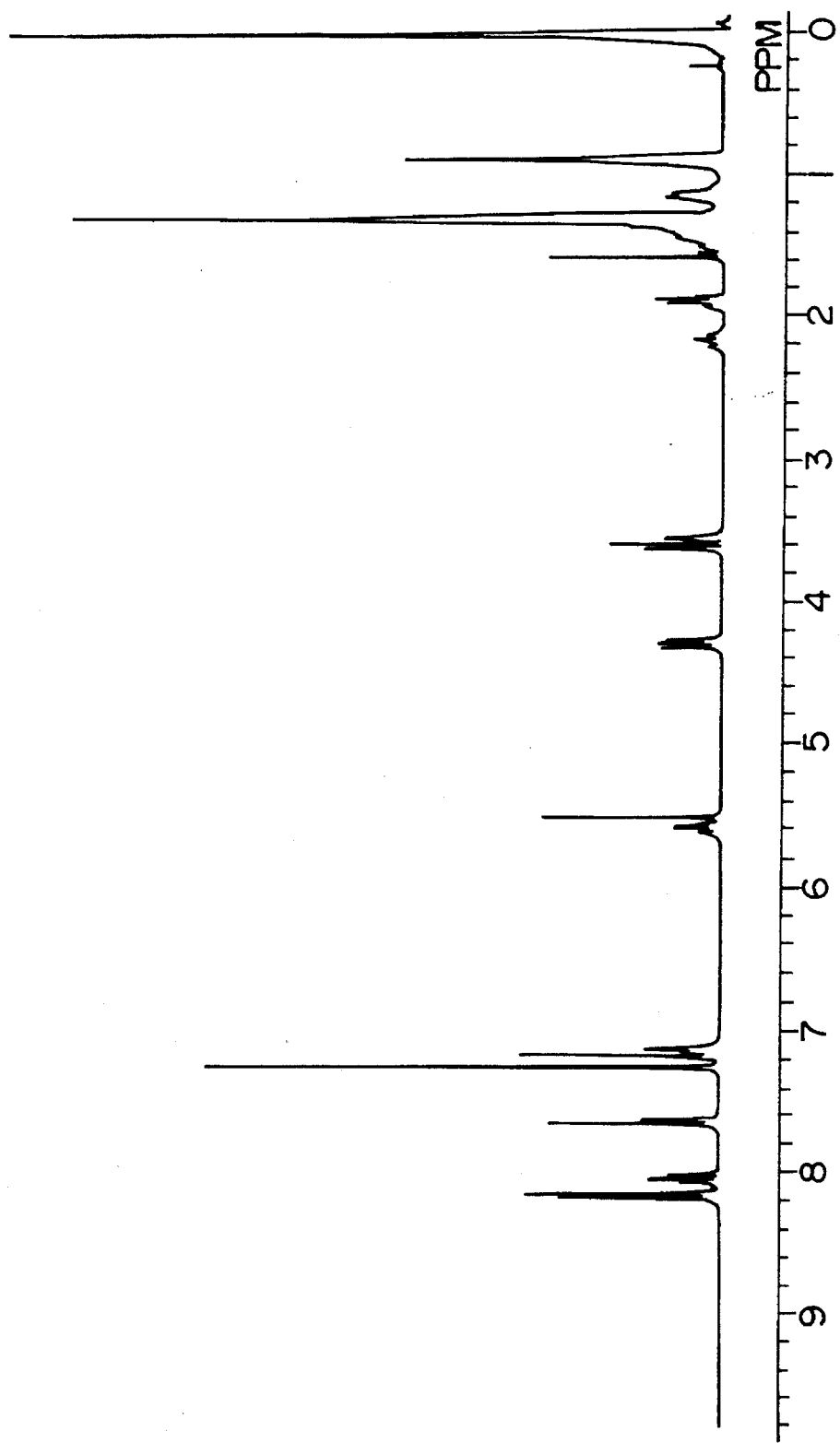
FIG. 7 is an NMR spectrum of the liquid crystal substance obtained in Example 5.

The NMR spectrum of the compound is shown in FIG. 7. The identification of the phases of the compound was conducted by texture observation and DSC.

The phase sequence of the compound was as follows. The compound was confirmed to be a liquid crystal substance having an antiferroelectric phase.

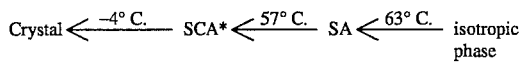

The compound was examined for optical response in the same manner as in Example 1 (8). As a result, the compound showed double hysteresis characteristic of an antiferroelectric phase at a temperature range of 57° C. to −4° C. The compound was also examined for response time in the same manner as in Example 1 (8). As a result, the response time at 28° C. was 30 microseconds from the antiferroelectric phase to the ferroelectric phase and 200 microseconds from the ferroelectric phase to the antiferroelectric phase, and the response was very quick.

EXAMPLE 6

Production of 3-fluoro-4-(1-ethyl-heptyloxycarbonyl)phenyl 4-(5-n-octyl-1,3-dioxan-2-yl)benzoate [a compound of general formula (1) wherein R=n-$C_8H_{17}$, X= shown in Table 1, Y=-$C_2H_5$, L=0, m=0 and n=6]

An intended compound was produced in the same manner as in Example 3 except that the R-(+)-1,1,1-trifluoro-7-ethoxy-2-heptanol used in Example 3 was replaced by S-(+)-3-nonanol.

Figure 8:
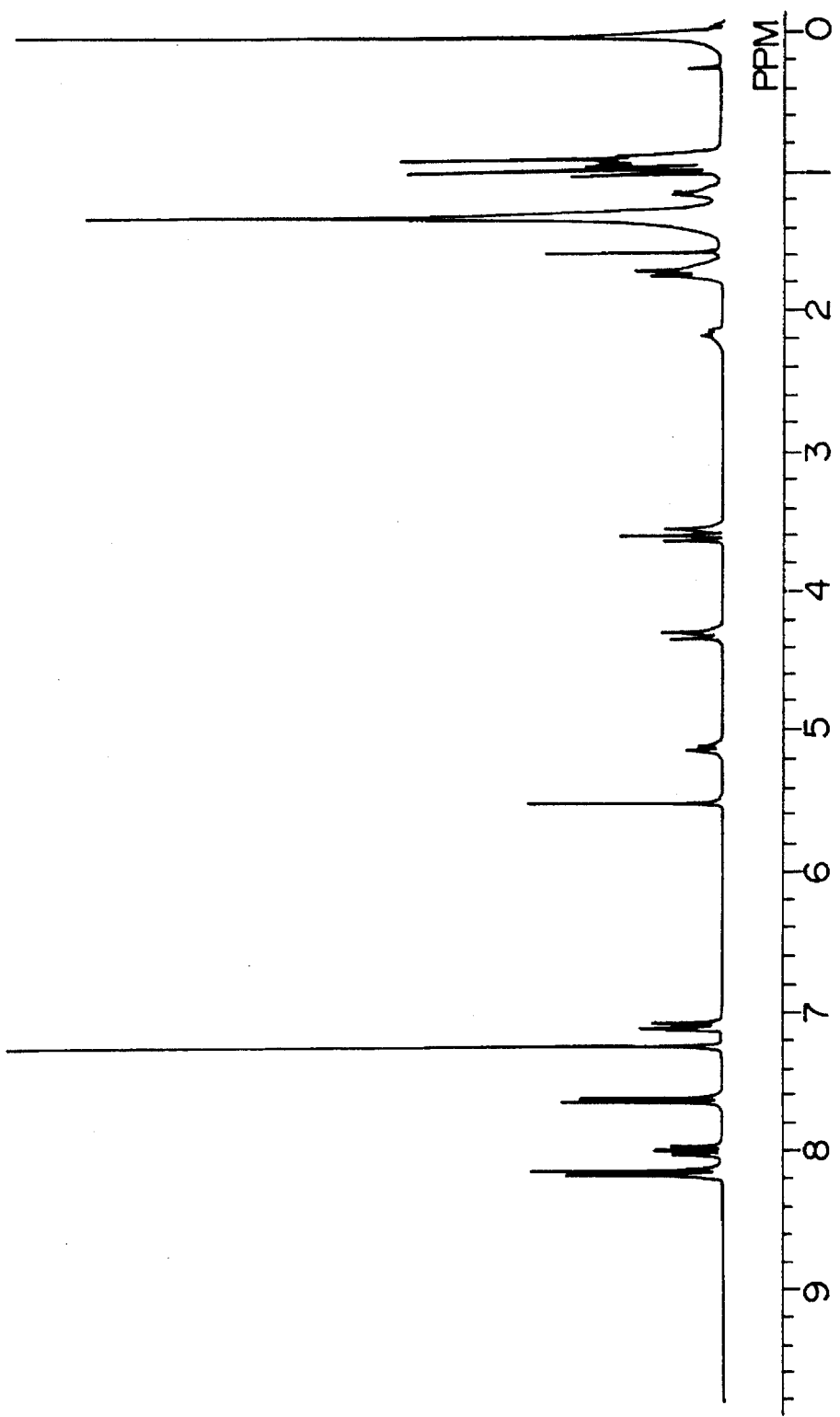
FIG. 8 is an NMR spectrum of the liquid crystal substance obtained in Example 6.

The NMR spectrum of the compound is shown in FIG. 8. The identification of the phases of the compound was conducted by texture observation and DSC.

The phase sequence of the compound was as follows. The compound was confirmed to be a liquid crystal substance having an antiferroelectric phase.

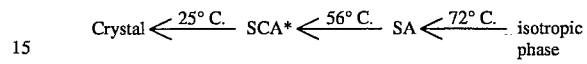

The compound was examined for optical response in the same manner as in Example 1 (8). As a result, the compound showed double hysteresis characteristic of an antiferroelectric phase at a temperature range of 55° C. to 25° C. The compound was also examined for response time in the same manner as in Example 1 (8). As a result, the response time at 28° C. was 200 microseconds from the antiferroelectric phase to the ferroelectric phase and 230 microseconds from the ferroelectric phase to the antiferroelectric phase, and the response was relatively quick.

COMPARATIVE EXAMPLE 2

Production of 2-fluoro-4-(1-trifluoromethyl-8 -ethoxy-octyloxycarbonyl)phenyl 4-(5-n-octyl-1,3-dioxan-2-yl)benzoate [a compound of general formula (1) wherein R =n-$C_8H_{17}$, X=shown in Table 2, Y=-$CF_3$, L=7, m=1 and n=2]

An intended compound was produced in the same manner as in Example 1 except that the 4-acetoxy-benzoic acid used in Example 1 was replaced by 3-fluoro-4-acetoxybenzoic acid.

Figure 9:
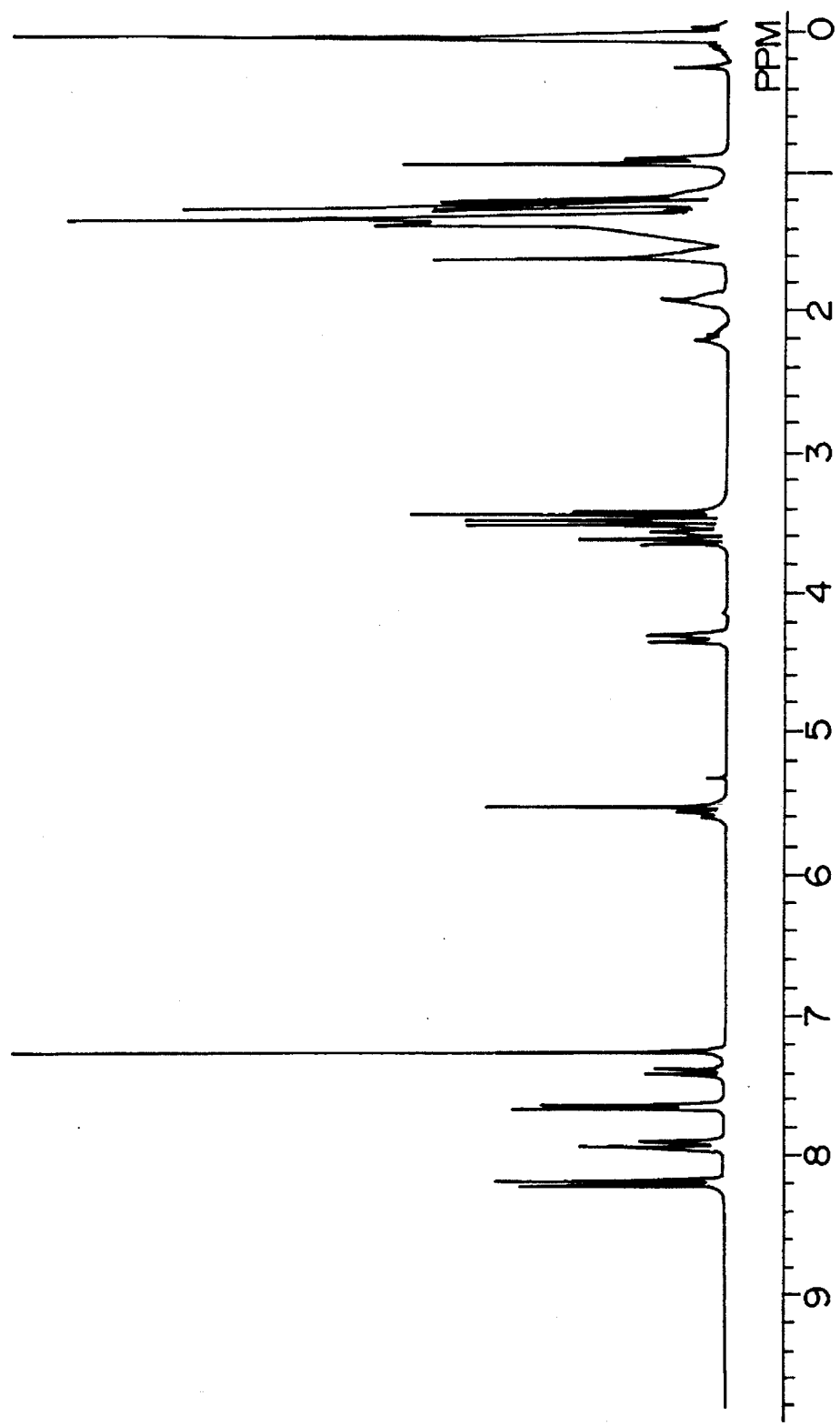
FIG. 9 is an NMR spectrum of the liquid crystal substance obtained in Comparative Example 2.

The NMR spectrum of the compound is shown in FIG. 9. The identification of the phases of the compound was conducted by texture observation and DSC.

The phase sequence of the compound was as follows. The compound had an antiferroelectric phase.

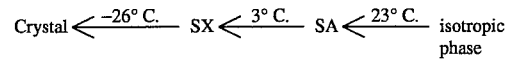

COMPARATIVE EXAMPLE 3

Production of 2-fluoro-4-(1-trifluoromethylheptyloxycarbonyl)phenyl 4-(5-n-octyl-1,3-dioxan-2-yl)-benzoate [a compound of general formula (1) wherein R= n-$C_8H_{17}$, X=shown in Table 2, Y=-$CF_3$, L=0, m=0 and n=6]

An intended compound was produced in the same manner as in Comparative Example 2 except that the R-(+)-1,1,1-trifluoro-9-ethoxy-2-nonanol used in Comparative Example 2 was replaced by R-(+)-1,1,1-trifluoro-2-octanol.

Figure 10:
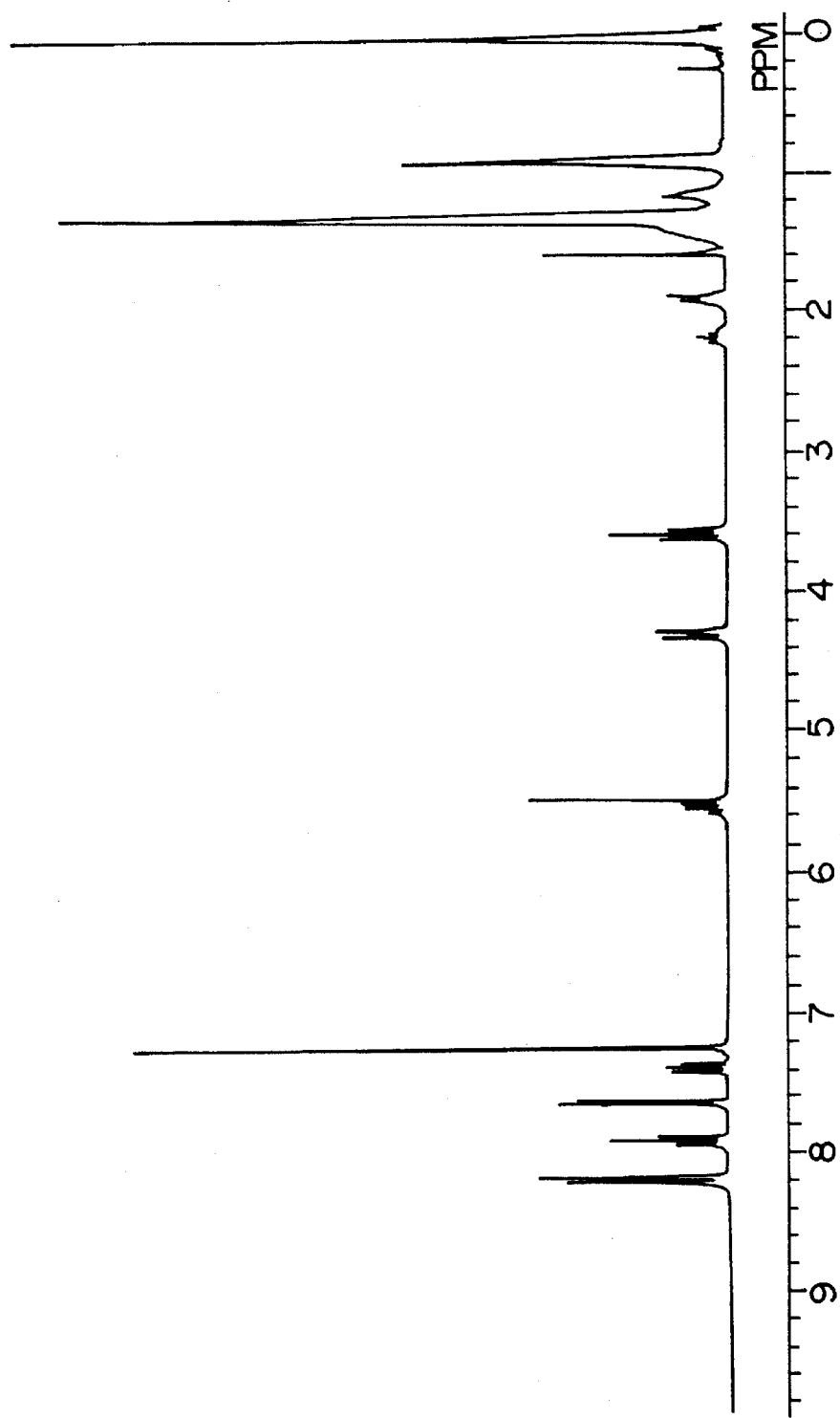
FIG. 10 is an NMR spectrum of the liquid crystal substance obtained in Comparative Example 3.

The NMR spectrum of the compound is shown in FIG. 10. The identification of the phases of the compound was conducted by texture observation and DSC.

The phase sequence of the compound was as follows. The compound had no antiferroelectric phase.

Crystal ⇌ 9° C. SA ⇌ 65° C. isotropic phase

COMPARATIVE EXAMPLE 4

Production of 2-fluoro-4-(1-ethyl-heptyloxycarbonyl)phenyl 4-(5-n-octyl-1,3-dioxan-2-yl)benzoate [a compound of general formula (1) wherein R=n-$C_8H_{17}$, X= shown in Table 2, Y=-$C_2H_5$, L=0, m=0 and n=6]

An intended compound was produced in the same manner as in Comparative Example 2 except that the R-(+)-1,1,1-trifluoro-9-ethoxy-2-nonanol used in Comparative Example 2 was replaced by S-(+)-3-nonanol.

Figure 11:
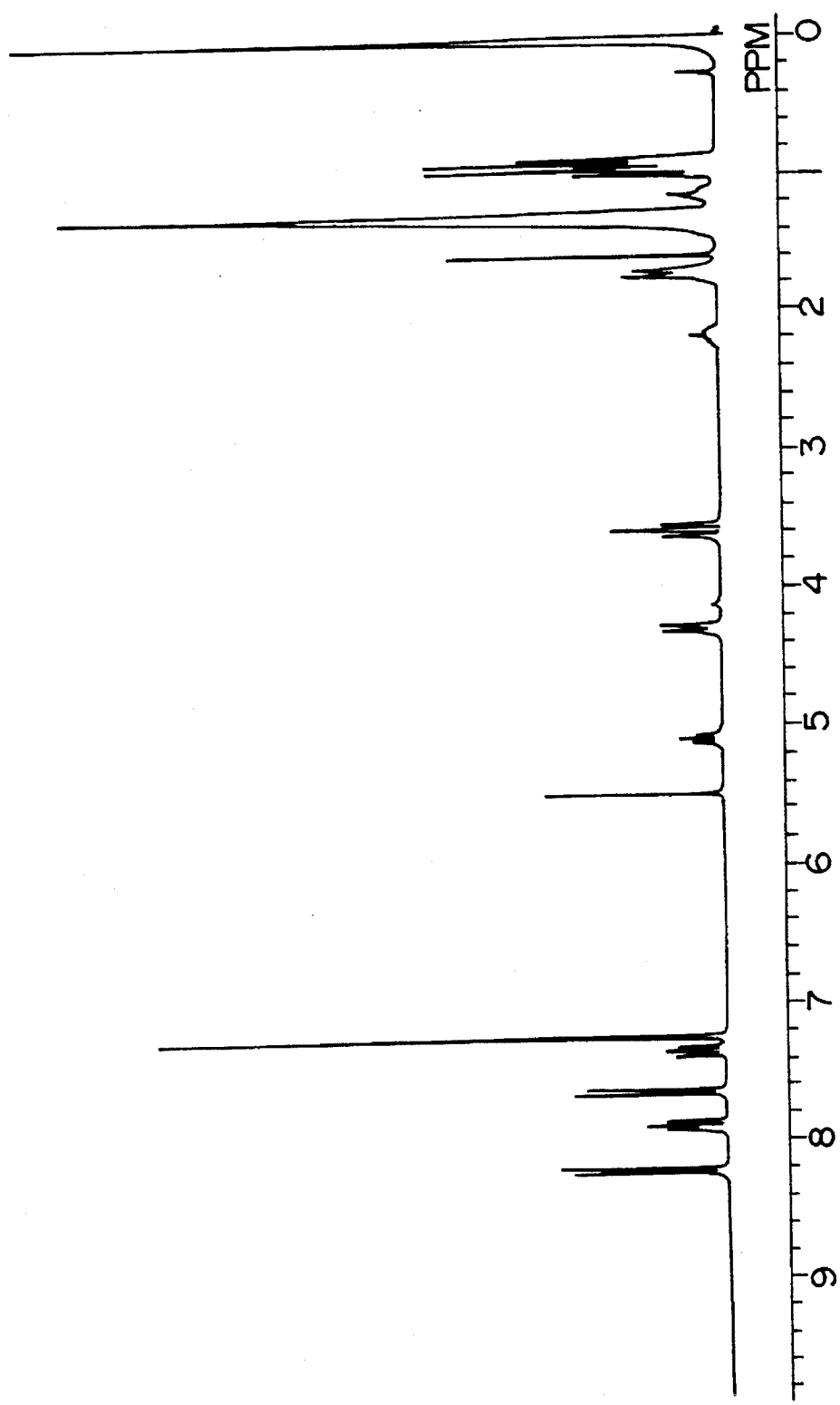
FIG. 11 is an NMR spectrum of the liquid crystal substance obtained in Comparative Example 4.

The NMR spectrum of the compound is shown in FIG. 11. The identification of the phases of the compound was conducted by texture observation and DSC.

The phase sequence of the compound was as follows. The compound had no antiferroelectric phase.

Crystal ⇌ 47° C. SA ⇌ 50° C. isotropic phase

EXAMPLE 7

Production of 4-(1-trifluoromethyl-7-ethoxyheptyloxycarbonyl)phenyl 4-(5-n-octyl-1,3-dioxan-2-yl)benzoate [a compound of general formula (1) wherein R= n-$C_9H_{19}$, X=shown in Table 1, Y=-$CF_3$, L=5, m=1 and n=2]

An intended compound was produced in the same manner as in Example 1 except that the 4-(5-octyl-1,3-dioxan-2-yl)benzoic acid used in Example 1 was replaced by 4-(5-nonyl-1,3-dioxan-2-yl)benzoic acid and the R-(+)-1,1,1-trifluoro-9-ethoxy-2-nonanol used in Example 1 was replaced by R-(+)-1,1,1-trifluoro-9-ethoxy-2-heptanol.

Figure 12:
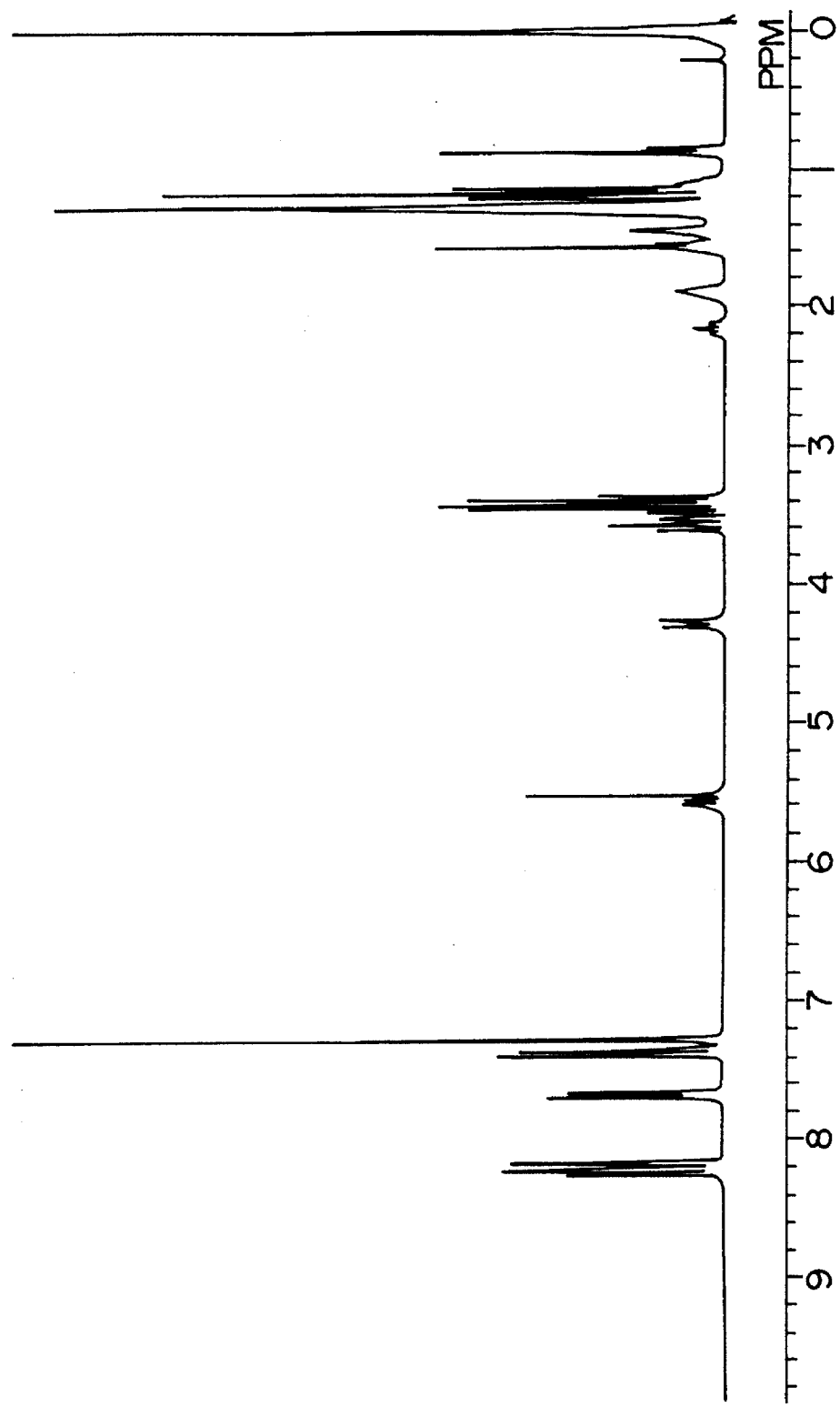
FIG. 12 is an NMR spectrum of the liquid crystal substance obtained in Example 7.

The NMR spectrum of the compound is shown in FIG. 12. The identification of the phases of the compound was conducted by texture observation and DSC.

The phase sequence of the compound was as follows. The compound was confirmed to be a liquid crystal substance having an antiferroelectric phase.

Crystal ⇌ ? SX ⇌ 14° C. SCA* ⇌ 51° C. SA ⇌ 56° C. isotropic phase

The compound was examined for optical response in the same manner as in Example 1 (8). As a result, the compound showed double hysteresis characteristic of an antiferroelectric phase at a temperature range of 50° C. to 14° C. The compound was also examined for response time in the same manner as in Example 1 (8). As a result, the response time at 25° C. was 42 microseconds from the antiferroelectric phase to the ferroelectric phase and 22 microseconds from the ferroelectric phase to the antiferroelectric phase, and the response was very quick.

EXAMPLE 8

Production of 3-fluoro-4-(1-trifluoromethyl-7-ethoxyheptyloxycarbonyl)phenyl 4-(5-n-octyl-1,3-dioxan- 2-yl)benzoate [a compound of general formula (1) wherein R=n-$C_9H_{19}$, X=shown in Table 1, Y=-$CF_3$, L=5, m=1 and n=2]

An intended compound was produced in the same manner as in Example 1 except that the 4-(5-octyl-1,3 -dioxan-2-yl)benzoic acid used in Example 1 was replaced by 4-(5-octyl-1,3-dioxan-2-yl)benzoic acid, the R-(+)- 1,1,1-trifluoro-9-ethoxy-2-nonanol used in Example 1 was replaced by R-(+)-1,1,1-trifluoro-7-ethoxy-2-heptanol and the 4-acetoxy-benzoic acid used in Example 1 was replaced by 4-acetoxy-fluorobenzoic acid.

Figure 13:
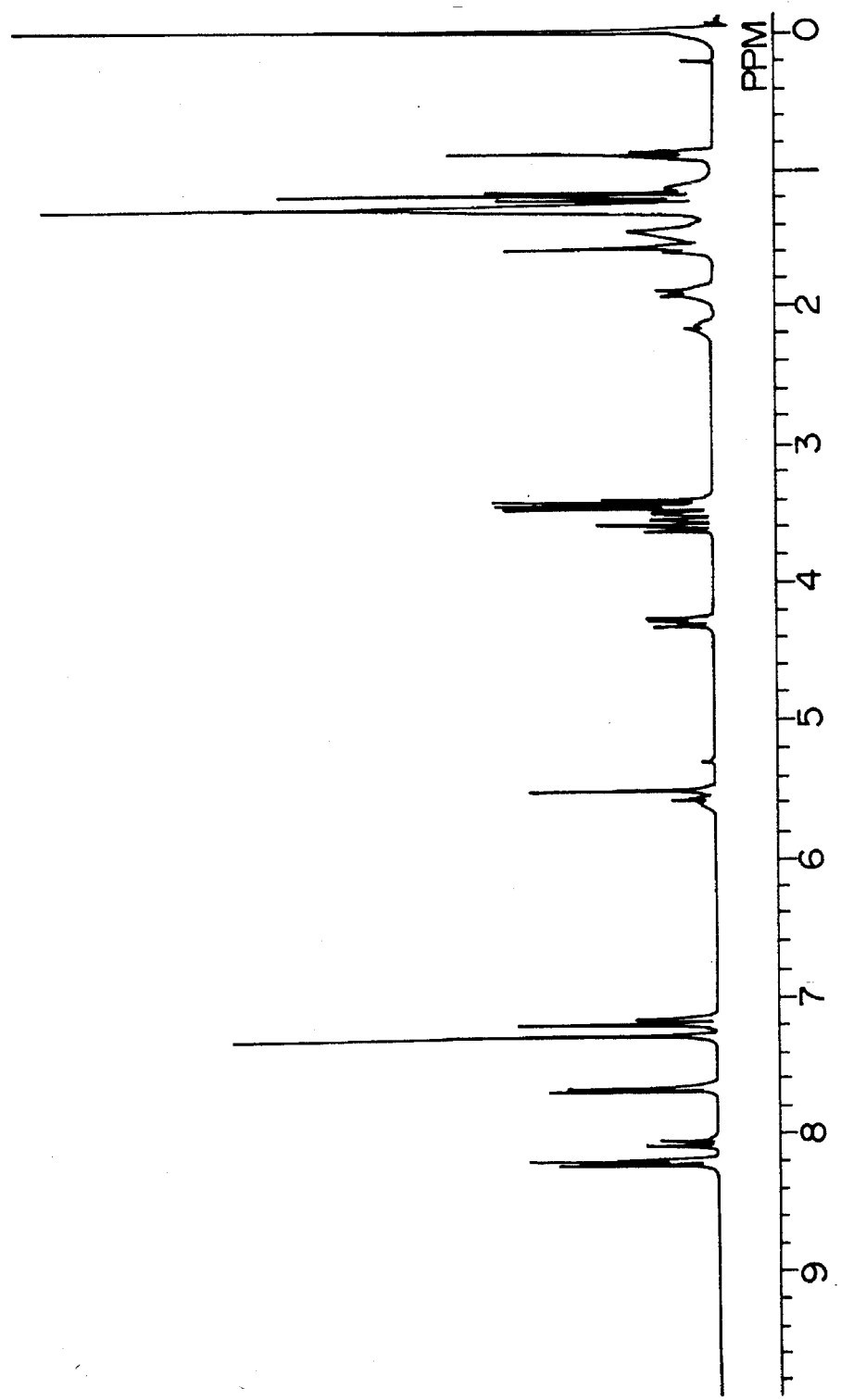
FIG. 13 is an NMR spectrum of the liquid crystal substance obtained in Example 8.

The NMR spectrum of the compound is shown in FIG. 13. The identification of the phases of the compound was conducted by texture observation and DSC.

The phase sequence of the compound was as follows. The compound was confirmed to be a liquid crystal substance having an antiferroelectric phase.

Crystal ⇌ −7° C. SCA* ⇌ 43° C. isotropic phase

The compound was examined for optical response in the same manner as in Example 1 (8). As a result, the compound showed double hysteresis characteristic of an antiferroelectric phase at a temperature range of 40° C. to −5° C. The compound was also examined for response time in the same manner as in Example 1 (8). As a result, the response time at 25° C. was 290 microseconds from the antiferroelectric phase to the ferroelectric phase and 950 microseconds from the ferroelectric phase to the antiferroelectric phase, and the response was very quick.

EXAMPLE 9

Production of 3-fluoro-4-(1-trifluoromethylheptyloxycarbonyl)phenyl 4-(5-n-octyl-1,3-dioxan-2-yl)benzoate [a compound of general formula (1) wherein R= n-$C_9H_{19}$, X=shown in Table 1, Y=-$CF_3$, L=0, m=0 and n=6]

An intended compound was produced in the same manner as in Example 1 except that the 4-(5-octyl-1,3 -dioxan-2-yl)benzoic acid used in Example 1 was replaced by 4-(5-nonyl-1,3-dioxan-2-yl)benzoic acid, the R-(+)- 1,1,1-trifluoro-9-ethoxy-2-nonanol used in Example 1 was replaced by R-(+)-1,1,1-trifluoro-2-octanol and the 4-acetoxy-benzoic acid used in Example 1 was replaced by 4-acetoxy-fluorobenzoic acid.

Figure 14:
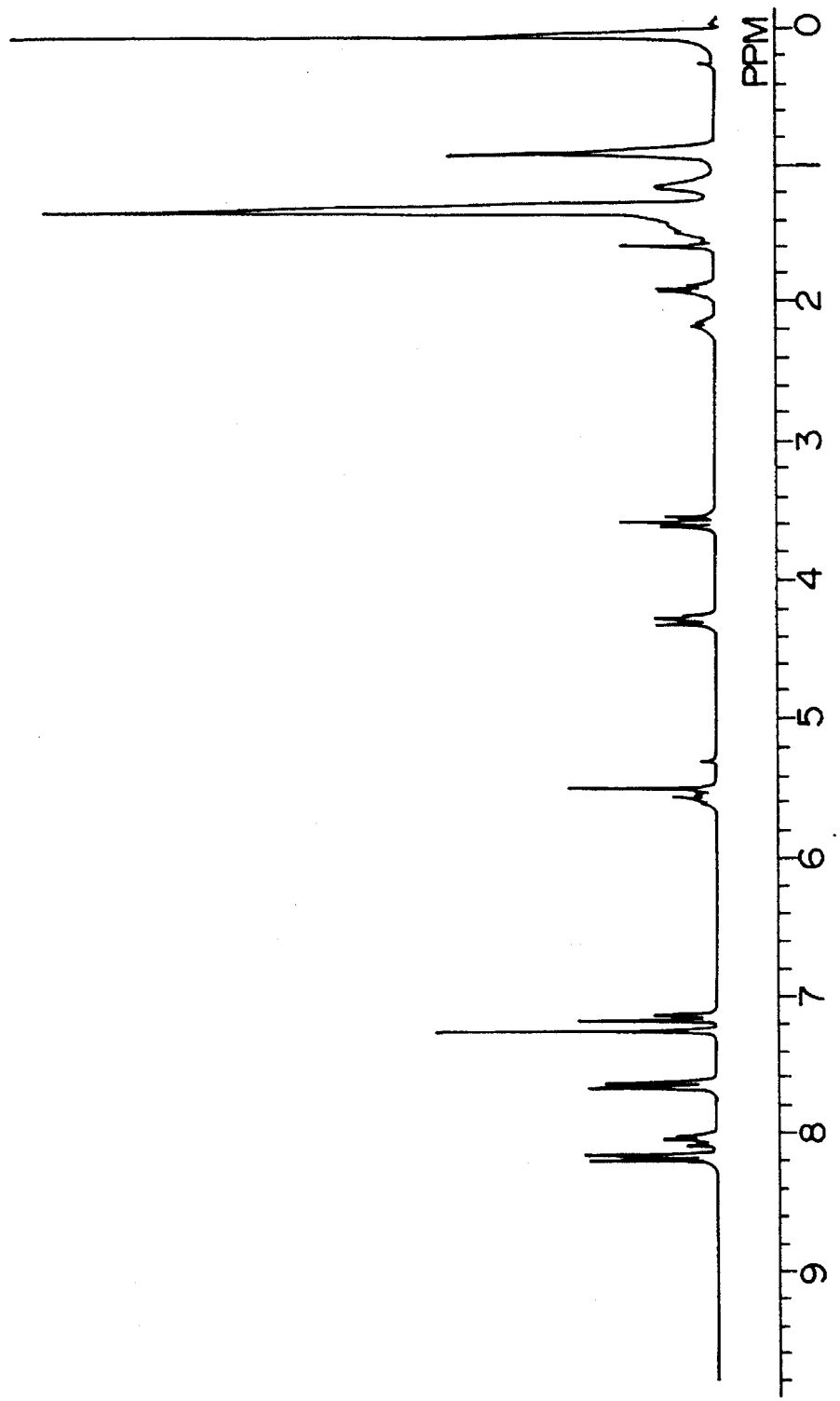
FIG. 14 is an NMR spectrum of the liquid crystal substance obtained in Example 9.

The NMR spectrum of the compound is shown in FIG. 14. The identification of the phases of the compound was conducted by texture observation and DSC.

The phase sequence of the compound was as follows. The compound was confirmed to be a liquid crystal substance having an antiferroelectric phase.

Crystal $\xleftarrow{23° C.}$ SCA* $\xleftarrow{63° C.}$ SA $\xleftarrow{65° C.}$ isotropic phase The compound was examined for optical response compound showed double hysteresis characteristic of an antiferroelectric phase at a temperature range of 63° C. to 22° C. The compound was also examined for response time in the same manner as in Example 1 (8). As a result, the response time at 43° C. was 136 microseconds from the antiferroelectric phase to the ferroelectric phase and 153 microseconds from the ferroelectric phase to the antiferroelectric phase, and the response was very quick.

TABLE 1

| No. of Example | X |
|---|---|
| 1 | (phenyl) |
| 2 | (phenyl) |
| 3 | (fluorophenyl) |
| 4 | (fluorophenyl) |
| 5 | (fluorophenyl) |
| 6 | (fluorophenyl) |
| 7 | (phenyl) |
| 8 | (fluorophenyl) |
| 9 | (fluorophenyl) |

TABLE 2

| No. of Comparative Example | X |
|---|---|
| 1 | (phenyl) |
| 2 | (fluorophenyl) |
| 3 | (fluorophenyl) |
| 4 | (fluorophenyl) |

What is claimed is:

1. An antiferroelectric liquid crystal substance represented by the following general formula (1)

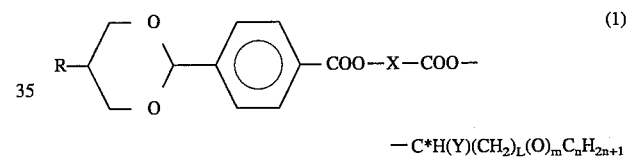

(1)

$$-C^*H(Y)(CH_2)_L(O)_mC_nH_{2n+1}$$

wherein R represents a straight-chain alkyl group of 6–10 carbon atoms; X represents

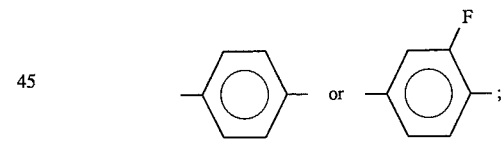

or ;

when X is

,

Y is any of $CH_3$, $CF_3$ and $C_2H_5$, L is 0 or an integer of 5 to 8, m is 0 or 1, and n is an integer of 1 to 10; when X is, Y is $CH_3$ or $C_2H_5$, and (1) when Y is $CH_3$, L is 0 or an integer of 5 to 8, m is 0 or 1, and n is an integer of 1 to 10 and (2) when Y is $C_2H_5$, L is 0, m is 0, and n is an integer of 4–10.

2. An antiferroelectric liquid crystal substance represented by the following general formula (1)

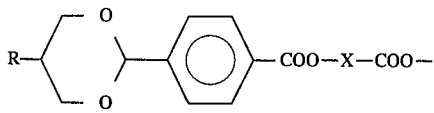  (1)

$-C^*H(Y)(CH_2)_L(O)_m C_n H_{2n+1}$ wherein R represents a straight-chain alkyl group of 6–10 carbon atoms; X represents

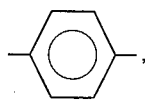,

Y is $CH_3$ or $C_2H_5$, and (1) when Y is $CH_3$, L is 0 or an integer of 5 to 8, m is 0 or 1, and n is an integer of 1 to 10 and (2) when Y is $C_2H_5$, L is 0, m is 0, and n is an integer of 4–10.

3. The antiferroelectric liquid crystal compound according to claim 2 wherein Y is $CH_3$.

4. The antiferroelectric liquid crystal substance of claim 2 wherein Y is $CH_3$, L is 0 or an integer of 5 to 8, m is 0 or 1, and n is an integer of 1 to 10.

5. The antiferroelectric liquid crystal substance of claim 2 wherein Y is $C_2H_5$, L is 0, m is 0 and n is an integer of 4 to 10.

6. An antiferroelectric liquid crystal substance represented by the following general formula (1)

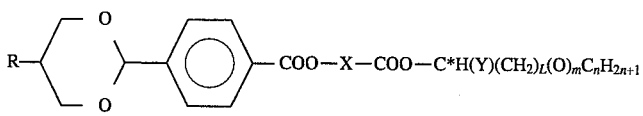  (1)

wherein R represents a straight-chain alkyl group of 6–10 carbon atoms; X represents

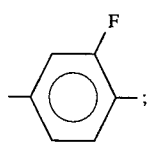;

Y is any of $CH_3$, $CF_3$ and $C_2H_5$, L is 0 or an integer of 5 to 8, m is 0 or 1, and n is an integer of 1 to 10.

7. The antiferroelectric liquid crystal compound according to claim 6 wherein Y is $CH_3$.

8. The antiferroelectric liquid crystal compound according to claim 6 wherein Y is $CF_3$.

9. The antiferroelectric liquid crystal compound according to claim 6 wherein Y is $C_2H_5$.

10. The antiferroelectric liquid crystal compound according to claim 8 wherein L is 0.

11. The antiferroelectric liquid crystal compound according to claim 9 wherein L is 0.

12. The antiferroelectric liquid crystal compound according to claim 6 wherein L is 0.

13. The antiferroelectric liquid crystal compound according to claim 12 wherein m is 0.

14. The antiferroelectric liquid crystal compound according to claim 12 wherein m is 1.

15. The antiferroelectric liquid crystal compound according to claim 6 wherein L is 5 to 8 and m is 1.

16. The antiferroelectric liquid crystal substance of claim 6 wherein L is an integer of 5 to 8 and m is 1.

17. The antiferroelectric liquid crystal substance of claim 6 wherein L is 0 and m is 0.

18. An antiferroelectric liquid crystal device containing an antiferroelectric liquid crystal substance represented by the following general formula (1)

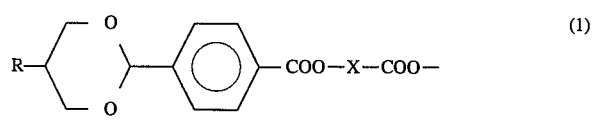  (1)

$-C^*H(Y)(CH_2)_L(O)_m C_n H_{2n+1}$ wherein R represents a straight-chain alkyl group of 6–10 carbon atoms; X represents (1)

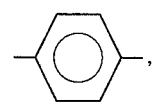,

Y is $CH_3$ or $C_2H_5$, and (1) when Y is $CH_3$, L is 0 or an integer of 5 to 8, m is 0 or 1, and n is an integer of 1 to 10 and (2) when Y is $C_2H_5$, L is 0, m is 0, and n is an integer of 4–10.

19. The antiferroelectric liquid crystal substance of claim 18 wherein Y is $CH_3$, L is 0 or an integer of 5 to 8, m is 0 or 1, and n is an integer of 1 to 10.

20. The antiferroelectric liquid crystal substance of claim 18 wherein Y is $C_2H_5$, L is 0, m is 0 and n is an integer of 4 to 10.

21. An antiferroelectric liquid crystal device containing an antiferroelectric liquid crystal substance represented by the following general formula (1)

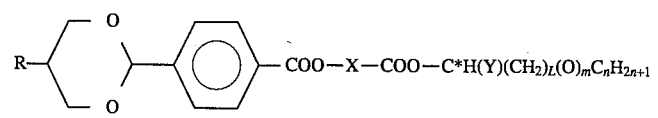  (1)

wherein R represents a straight-chain alkyl group of 6–10 carbon atoms; X represents

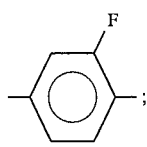

Y is any of $CH_3$, $CF_3$ and $C_2H_5$, L is 0 or an integer of 5 to 8, m is 0 or 1, and n is an integer of 1 to 10.

22. The antiferroelectric crystal substance of claim 21 wherein L is an integer of 5 to 8 and m is 1.

23. The antiferroelectric crystal substance of claim 21 wherein L is 0 and m is 0.

24. An antiferroelectric liquid crystal substance represented by the following formula

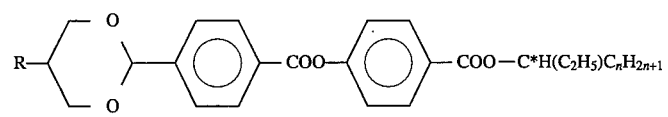

wherein R represents a straight-chain alkyl group of 6–10 carbon atoms and n is an integer of 4 to 10.

* * * * *